United States Patent
Fujita et al.

(10) Patent No.: US 11,517,599 B2
(45) Date of Patent: Dec. 6, 2022

(54) COMPOSITION FOR TREATING, PREVENTING, AMELIORATING OR SUPPRESSING CANCER OR INHIBITING CANCER METASTASIS

(71) Applicants: THE RITSUMEIKAN TRUST, Kyoto (JP); RESPECT CO., LTD., Otsu (JP)

(72) Inventors: Takashi Fujita, Kusatsu (JP); Sadanori Ito, Otsu (JP)

(73) Assignee: RESPECT CO., LTD., Otsu (JP)

( * ) Notice: Subject to any disclaimer, the term of this patent is extended or adjusted under 35 U.S.C. 154(b) by 51 days.

(21) Appl. No.: 17/255,559

(22) PCT Filed: Jun. 24, 2019

(86) PCT No.: PCT/JP2019/024879
§ 371 (c)(1),
(2) Date: Dec. 23, 2020

(87) PCT Pub. No.: WO2020/004299
PCT Pub. Date: Jan. 2, 2020

(65) Prior Publication Data
US 2021/0268052 A1    Sep. 2, 2021

(30) Foreign Application Priority Data
Jun. 25, 2018   (JP) .............................. JP2018-120159

(51) Int. Cl.
A61K 36/064    (2006.01)
A23L 33/145    (2016.01)

(52) U.S. Cl.
CPC ........... *A61K 36/064* (2013.01); *A23L 33/145* (2016.08); *A61K 2236/19* (2013.01)

(58) Field of Classification Search
CPC .. A61K 36/064; A61K 2236/19; A61K 36/00; A23L 33/145
See application file for complete search history.

(56) References Cited

U.S. PATENT DOCUMENTS 6,355,474 B1   3/2002  Hidvegi et al.
6,395,315 B1   5/2002  Matsurra

FOREIGN PATENT DOCUMENTS

| JP | 2006-298871 A | 11/2006 |
|---|---|---|
| JP | 2011-236245 A | 11/2011 |
| WO | 98/01042 A1 | 1/1998 |
| WO | 2005/032568 A1 | 4/2005 |

OTHER PUBLICATIONS

Lu et al., "Inhibitory effects of vegetable and fruit ferment liquid on tumor growth in Hepatoma-22 inoculation model", Asia Pac J Clin Nutr 2007; 16 (Suppl 1):443-446 (Year: 2007).*
International Search Report dated Sep. 3, 2019 for International Patent Application No. PCT/JP2019/024879, 4 pages with English translation.
Ohgidani et al., "Anticancer Effects of Residual Powder from Barley-Shochu Distillation Remnants against the Orthotopic Xenograft Mouse Models of Hepatocellular Carcinoma in Vivo", Biol. Pharm. Bull, 2012, vol. 35, No. 6, pp. 984-987.
Kim et al., "In Vitro Antioxidant and Anticancer Activities of Extracts from a Fermented Food", Journal of Food Biochemistry, 2003, vol. 7, No. 6, pp. 449-459.
Marotta et al., "Inhibition of Human Breast Cancer Cell Growth and Enzymatic Activity by a Fermented Nutraceutical: An in Vitro and in Vivo Study", Annals of the New York Academy of Sciences, 2009, vol. 1155, No. 1, pp. 273-277.
Topalian et al., "Safety, Activity, and Immune Correlates of Anti-PD-1 Antibody in Cancer", The New England Journal of Medicine, 2012, vol. 366, No. 26, pp. 2443-2454.
Shoji Goto, "Natural Fermantation of Grape Wine and Pure Cultured Yeast", New Food Industry, 1996, vol. 38, No. 1, pp. 65-68. (See p. 3 of the translation of Japanese Office Action dated Sep. 3, 2019 for a concise explanation of the relevance of this document, which is referred to as Document 7 in the Office Action).
Japanese Office Action dated Sep. 3, 2019 for corresponding Japanese Patent Application No. 2018-120159, 7 pages with English translation.
Ito Premium Enzyme Brochure, 2017, November Issue, 1 page. (See pp. 1-3 of the translation of Japanese Office Action dated Dec. 10, 2019 for a concise explanation of the relevance of this document, which is referred to as Document 8 in the Office Action).
Japanese Office Action dated Dec. 10, 2019 for corresponding Japanese Patent Application No. 2018-120159, 6 pages with English translation.

* cited by examiner

*Primary Examiner* — Ruth A Davis
(74) *Attorney, Agent, or Firm* — MH2 Technology Law Group, LLP

(57) ABSTRACT

The disclosure is a composition for treating, preventing, ameliorating, or suppressing cancer, or inhibiting cancer metastasis, comprising a plant fermentation extract as an active ingredient, wherein the plant fermentation extract comprises a yeast that is viable in an environment at pH 1 and that is capable of forming spores in a complete medium.

6 Claims, 3 Drawing Sheets

COMPOSITION FOR TREATING, PREVENTING, AMELIORATING OR SUPPRESSING CANCER OR INHIBITING CANCER METASTASIS

CROSS-REFERENCE TO RELATED APPLICATIONS

This application is a U.S. National Stage application of PCT/JP2019/024879, filed 24 Jun. 2019, which claims priority to Japanese Application No. 2018-120159, filed 25 Jun. 2018, the entire disclosures of which are incorporated herein by reference in their entireties.

TECHNICAL FIELD

The present invention relates to a composition for treating, preventing, ameliorating, or suppressing cancer, or inhibiting cancer metastasis.

BACKGROUND ART

Over the past few decades, cytotoxic chemotherapy has dominated the systematic management of cancer according to the maximum tolerated dose (MTD). In MTD therapy, in order to achieve the best therapeutic effects, the administration of the highest tolerable dosage of a drug to a patient is required. Due to low tumor selectivity, MTD treatments cannot be protracted in order to allow recovery of healthy tissue and to reduce myelosuppression. Rapid tumor growth and metastasis during the therapeutic breaks may cause a burst of cancer cell proliferation accompanied by chemoresistance and accelerated angiogenesis. Accordingly, a reappraisal of advanced-stage cancer management is ongoing, moving from the maximum tolerable dose to the minimum effective dose, by combining treatment with a supplement. As a typical example, although an anti-PD-1 antibody has a very rough dose-response relationship with regard to efficacy and safety, a clear "dose-response curve" is not likely to be observed, and there is a case in which a very small dose of the anti-PD-1 antibody provides a safe and effective treatment (Non-patent Literature 1).

CITATION LIST

Non-Patent Literature

NPL 1: Topalian SL, et al. Safety, Activity, and Immune Correlates of Anti-PD-1 Antibody in Cancer. N Engl J Med 2012; 366: 2443-2454

SUMMARY OF INVENTION

Technical Problem

An object of the present invention is to provide a composition for treating, preventing, ameliorating, or suppressing cancer, or inhibiting cancer metastasis, wherein the composition can be used as a supplement (food) and has excellent anti-cancer and anti-metastasis effects.

Solution to Problem

The present inventors conducted extensive research to achieve the above object. As a result, they found that a plant fermentation extract obtained by fermentation of a plant extract using a yeast that is viable in an environment at pH 1 and that is capable of forming spores in a complete medium has excellent anti-cancer and anti-metastasis effects.

Based on the above findings, the present inventors conducted further research, and accomplished the present invention. The present invention provides a composition for treating, preventing, ameliorating, or suppressing cancer, or inhibiting cancer metastasis.

Item 1. A composition for treating, preventing, ameliorating, or suppressing cancer, or inhibiting cancer metastasis, comprising a plant fermentation extract as an active ingredient,
wherein the plant fermentation extract comprises a yeast that is viable in an environment at pH 1, and that is capable of forming spores in a complete medium.

Item 2. The composition according to Item 1, wherein the plant fermentation extract is obtained by fermenting a plant extract using the yeast.

Item 3. The composition according to Item 1 or 2, wherein the yeast belongs to the genus *Saccharomyces cerevisiae*.

Item 4. The composition according to any one of Items 1 to 3, wherein the composition is a food or drink, or a drug.

Item 5. A method for treating, preventing, ameliorating, or suppressing cancer, or inhibiting cancer metastasis, comprising administering an effective amount of a plant fermentation extract to a mammal,
wherein the plant fermentation extract comprises a yeast that is viable in an environment at pH 1, and that is capable of forming spores in a complete medium.

Item 6. The method according to Item 5, wherein the plant fermentation extract is obtained by fermenting the plant extract using the yeast.

Item 7. The method according to Item 5 or 6, wherein the yeast belongs to the genus *Saccharomyces cerevisiae*.

Item 8. Use of a plant fermentation extract in the production of a composition for treating, preventing, ameliorating, or suppressing cancer, or inhibiting cancer metastasis,
wherein the plant fermentation extract comprises a yeast that is viable in an environment at pH 1 and that is capable of forming spores in a complete medium.

Item 9. The use according to Item 8, wherein the plant fermentation extract is obtained by fermenting a plant extract using the yeast.

Item 10. The use according to Item 8 or 9, wherein the yeast belongs to the genus *Saccharomyces cerevisiae*.

Item 11. The use according to any one of Items 8 to 10, wherein the composition is a food or drink, or a drug.

Advantageous Effects of Invention

Since the plant fermentation extract of the present invention has excellent anti-cancer and anti-metastatic effects, it is useful as an active ingredient of a composition for treating, preventing, ameliorating, or suppressing cancer, or inhibiting cancer metastasis.

The plant fermentation extract of the present invention is a natural product, and is highly safe because it is produced by fermenting a plant extract; thus, it is usable as a supplement (food).

DESCRIPTION OF EMBODIMENTS

Figure 1:
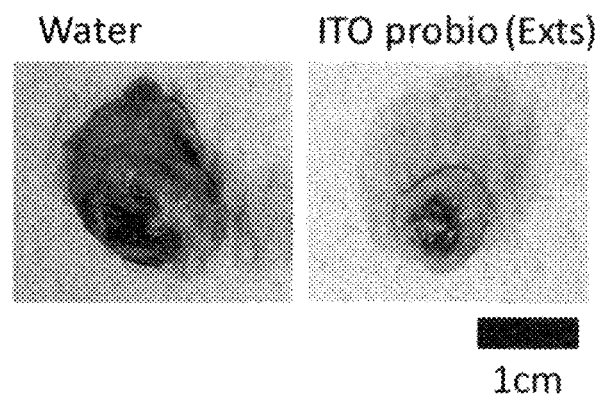
FIG. 1 shows photographs showing transplanted tumors after the transplantation of 4T1-luc cells into mice.

The present invention is explained in detail below.

In this specification, the term "comprise" also includes the meanings of "essentially consist of" and "consist of."

The composition for treating, preventing, ameliorating, or suppressing cancer, or inhibiting cancer metastasis of the present invention (sometimes referred to as the "composition of the present invention") comprises a plant fermentation extract as an active ingredient. The plant fermentation extract comprises a yeast that is viable in an environment at pH 1, and that is capable of forming spores in a complete medium. The plant fermentation extract is preferably produced by fermenting the plant extract using a yeast that is viable in an environment at pH 1, and that is capable of forming spores in a complete medium.

In the present invention, "viable in an environment at pH 1" means that the yeast is viable in an environment at pH 1 preferably for 3 hours or more, more preferably for 4 hours or more, and even more preferably for 5 hours or more. Such high acid resistance allows the yeast to reach the intestines alive when the yeast is ingested by mouth, without being killed in the stomach.

In the present invention, "capable of forming spores in a complete medium" means that when the yeast is cultured in a complete medium such as a YPD medium, it preferably shows a spore-forming rate of 10% or more, more preferably 50% or more, and even more preferably 70% or more. Thus, forming spores in a complete medium means forming spores in a product; therefore, the product has high stability.

The plant that is a raw material of the plant fermentation extract of the present invention is not particularly limited. Examples include vegetables, such as green perilla, red perilla, melon, *Perilla frutescens*, barley grass, turnip, squash, cauliflower, cabbage, cucumber, kale, bitter melon, burdock, celery, komatsuna (Japanese mustard spinach), zucchini, garland chrysanthemum, ginger, Japanese white radish, onion, bok Choy (Chinese cabbage), tomato, eggplant, Chinese chive, carrot, garlic, leek, parsley, green pepper, butterbur sprout, broccoli, spinach, mizuna (potherb mustard), Brussels sprout, mulukhiyah, and mugwort; fruits, such as akebi, strawberry, fig, persimmon, kumquat, mulberry, citrus sudachi, Chinese citron, citrus hassaku, blueberry, mandarin orange, yuzu, lemon, and blackberry (wild strawberry); beans, such as soybeans; grains, such as brown rice; sugars, such as brown sugar; seaweeds, such as kombu (Japanese seaweed) and *Fucus distichus*; mushrooms, such as agaricus, *Fuscoporia obliqua*, shiitake mushroom, and maitake mushroom; and the like. It is preferable to use all of the above-mentioned products (59 kinds) as raw-material vegetables. These 59 vegetables include various types of cruciferous vegetables. It is desirable to use, as raw-material vegetables, vegetables that are free of chemical fertilizers and pesticides, vegetables that are harvested in season, and vegetables that are grown in open air. Examples of vegetables free of chemical fertilizers and pesticides include agricultural products that meet the standards of Organic JAS.

The method for extracting a vegetable extract from a raw-material vegetable is not particularly limited, and various known methods can be used. Of these, it is preferable to extract a vegetable extract by osmotic extraction, particularly osmotic extraction using brown sugar. In the extraction process, lactic acid fermentation by lactic acid bacteria attached to a vegetable occurs, which reduces the pH. As a result, the growth of miscellaneous bacteria can be inhibited.

After a vegetable extract was obtained from a raw-material vegetable, the vegetable extract was subjected to fermentation using yeast. As the yeast to be used for fermentation, yeast that is viable in an environment at pH 1 and that is capable of forming spores in a complete medium is preferable. Of such yeast, yeast belonging to the genus *Saccharomyces cerevisiae* is particularly preferable. The use of such yeast for fermentation allows the yeast to be included in the final product. The inclusion of the yeast allows the yeast to reach the intestine alive without being killed in the stomach when the product is ingested. In addition, the yeast forms spores in the product, which makes the product highly stable. Since the yeast has high acid resistance, it is viable even when the vegetable extract has a low pH, as mentioned above; and fermentation can be performed. The yeast used for fermentation should be yeast with dietary experience.

Fermentation can be performed by an ordinal method. Examples of the operation in the fermentation include adjusting the conditions of temperature, pH, humidity, and the like to the ranges in which the fermentation is suitably performed; suitably performing stirring; etc. The duration of the fermentation is not particularly limited. It is preferably 3 months or more, more preferably 6 months or more, even more preferably 9 months or more, still even more preferably 1 year or more, particularly preferably 2 years or more, and most preferably 3 years or more.

As the plant fermentation extract of the present invention, a commercially available product sold by Respect. Co., Ltd can be used.

The proportion of the plant fermentation extract in the composition for treating, preventing, ameliorating, or suppressing cancer, or inhibiting cancer metastasis of the present invention is, for example, 0.01 to 99 mass %, 1 to 80 mass %, or 10 to 70 mass %.

A known ingredient other than the plant fermentation extract can be suitably mixed with the composition of the present invention, as long as the effect of the present invention is not impaired.

The composition of the present invention can be used as a food or drink (particularly a food or drink having the goal, inter alia, of maintaining or promoting health (e.g., health foods, functional foods, dietary supplements, supplements, Foods for Specified Health Uses, Foods with Nutrient Function Claims, or Foods with Nutrient Function Claims)), a drug (including quasi-drugs), or the like. The composition of the present invention also includes the meaning of an additive that imparts effects of treating, preventing, ameliorating, or suppressing cancer, or inhibiting cancer metastasis.

For the food or drink mentioned above, the plant fermentation extract may be used as is. If necessary, vitamins, flavonoids, minerals, quinones, polyphenols, amino acids, nucleic acids, essential fatty acids, coolants, binders, sweeteners, colorants, flavors, stabilizers, preservatives, disintegrants, lubricants, slow-release modifiers, surfactants, dissolving agents, wetting agents, or the like can be added.

Examples of the food or drink include various food or drink that can be ingested by animals (including humans).

The kind of food or drink is not particularly limited. Examples include milk products; fermented foods (e.g., yogurt and cheese); beverages (e.g., soft drinks such as coffee, juice, and tea beverages; milk beverages; lactic acid bacterium beverages, lactic acid bacterium-containing beverages; yogurt beverages; carbonated beverages; alcohols, such as sake, Western liquors, and fruit liquors); spreads (e.g., custard cream); pastes (e.g., fruit pastes); confectioneries (e.g., chocolate, doughnuts, pies, cream puffs, gum, candies, jelly, cookies, cakes, and pudding); Japanese sweets (e.g., daifuku (soft rice cake with sweet bean), mochi, manjyu (steamed buns), kasutera (Castilla cakes), anmitsu (dessert including agar jelly, fruits, and red bean paste), and yokan (sweet-bean jelly); ice confectioneries (e.g., ice cream, popsicles, sherbet); foods (e.g., curry rice, beef bowl, porridge, miso soup, soup, meat sauce, pasta, pickles, and jam); seasonings (e.g., dressings, furikake (rice topping), umami seasoning, and soup base); etc.

The production method of the food or drink is not particularly limited, and the food or drink can be suitably produced by a known method.

The dosage unit form of the food or drink for use as a supplement is not particularly limited, and can be suitably selected. Examples include tablets, capsules, granules, liquids, dispersants, and the like.

The amount of intake of the food or drink may be suitably set according to various conditions, such as the weight, age, gender, symptoms, etc. of the person taking the product.

When the composition is prepared as a drug, the plant fermentation extract may be used as is. The plant fermentation extract may also be formed, with a non-toxic carrier acceptable in the drug, a diluent, or an excipient, into a preparation in the form of a tablet (including a bare tablet, sugar-coated tablet, film-coated tablet, foam tablet, chewable tablet, troche, or the like), capsule, pill, powders (dispersant), fine granules, granules, liquid, suspension, emulsion, syrup, paste, or the like, thus preparing a pharmaceutical preparation.

The dosage form of the drug may be suitably determined according to various conditions such as the patient's weight, age, gender, or symptoms.

The composition of the present invention, as explained above, can apply to mammals, including humans.

As shown in the Examples below, the present inventors have found that the plant fermentation extract of the present invention exhibits high anti-cancer and anti-metastatic effects.

Accordingly, since the plant fermentation extract of the present invention has excellent anti-cancer and anti-metastatic effects, it can be suitably used as an active ingredient of the composition for treating, preventing, ameliorating, or suppressing cancer, or inhibiting cancer metastasis.

Examples of cancers to which the composition of the present invention can be applied include stomach cancer, colorectal cancer (rectum cancer and colon cancer), small intestine cancer, liver cancer, pancreatic cancer, lung cancer, pharyngeal cancer, esophageal cancer, kidney cancer, gallbladder and bile duct cancer, head and neck cancer, bladder cancer, prostate cancer, breast cancer, uterine cancer (cervical cancer and uterine cancer), ovarian cancer, brain cancer, thymoma, leukemia, malignant lymphoma, and the like.

The plant fermentation extract of the present invention is a natural product and is highly safe because it is produced by fermenting the plant extract.

EXAMPLES

Examples are given below to explain the present invention in more detail. However, the present invention is not limited to these Examples.

The ITO Probio extracts (Respect. Co., Ltd) used in the following experiments correspond to the plant fermentation extract of the present invention.

Experimental Method

A 4T1 metastasis model was produced by implanting 4T1-luc cells (mouse Balb/cfC3H-derived breast cancer cells) ($10^5$ cells) into the second mammary skin of a Balb/c female mouse. The 4T1-luc cell line was selected as an in vivo model for the following two main reasons: 1) since a 4T1-derived tumor is malignant, high levels of proliferation, metastasis, and invasion are attained; and 2) since the luciferase activity is stable, observation of tumor growth and metastasis is possible.

22 days passed after the transplantation of 4T1-luc, and the mice were divided into three groups based on the tumor size. Treatments were then started. In Group 1, 1 mg/kg of doxorubicin (DOX) was intravenously injected into the tail vein as a positive control. A 2.5% ITO Probio extract dissolved in water was freely fed to the mice.

After the treatment was performed for 20 days, the mice were sacrificed, and organs including the lungs were removed and preserved. Part of the tissue was separated in units of about 10 mg, and the lysate was evaluated using a ONE-Glo Luciferase Assay System (Promega, Madison, Wis.). The luciferase activity was evaluated using a model TD20/20n luminometer (Turner BioSystems, Sunnyvale, Calif.).

Results

The results are shown in FIGS. 1 to 5.

Figure 2:
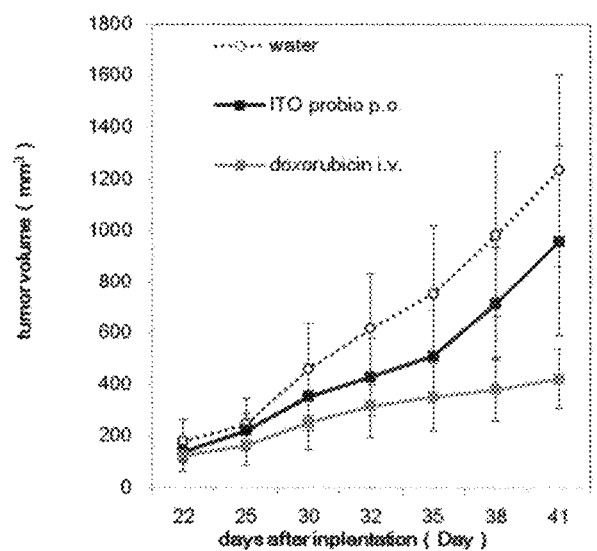
FIG. 2 is a graph showing a change in transplanted tumor volume ($mm^3$) after the transplantation of 4T1-luc cells into a mouse over time. The data represent mean±SEM. n=5
Figure 3:
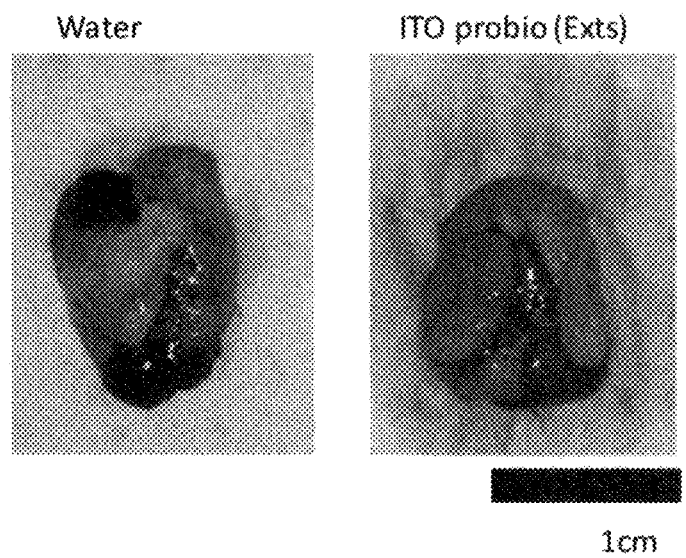
FIG. 3 shows photographs showing lungs after the transplantation of 4T1-luc cells into mice.
Figure 4:
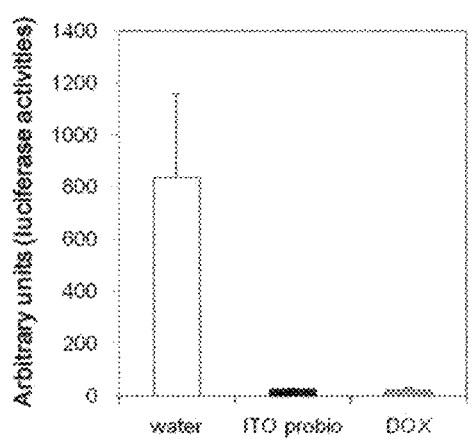
FIG. 4 is a graph showing luciferase activity in lungs after the transplantation of 4T1-luc cells into mice. The data represent mean±SEM. n=5
Figure 5:
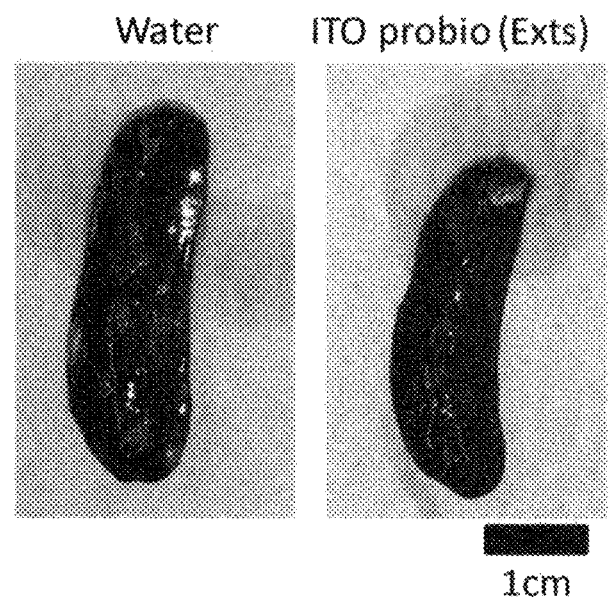
FIG. 5 shows photographs showing the spleen after the transplantation of 4T1-luc cells into mice.

FIGS. 1 and 2 indicate that the transplanted tumors in the ITO Probio extract administration group tend to shrink more than those in the water administration group. The tumor shrinkage tendency in the ITO Probio extract group was between that of the water administration group and that of the doxorubicin administration group. FIGS. 3 and 4 show that the effect of inhibition of pulmonary metastasis in the ITO Probio extract group was higher than that in the water administration group, and was comparable to that in the doxorubicin group (the white portion in FIG. 3 indicates pulmonary metastasis). FIG. 5 indicates that in the ITO Probio extract administration group, splenomegaly was reduced, as compared to that in the water administration group.

The results indicate that the ITO Probio extract suppresses tumor growth, and inhibits lung metastasis.

An enlarged spleen naturally causes pain. Such a state is referred to as splenomegaly. In splenomegaly, the spleen takes in platelets, red blood cells, etc., in the blood more than usual. Thus, the number of platelets and red blood cells in the blood is reduced. Additionally, the more the spleen takes in platelets and red blood cells, the larger the spleen becomes. Platelets and red blood cells that normally do not need to be taken into the spleen are taken in the spleen, and destroyed; additionally, too many platelets and red blood cells in the spleen lowers the function of the spleen. As a result, the function of the spleen is lowered, and immune strength etc. becomes weak.

The invention claimed is:

1. A method for treating, preventing, ameliorating, or suppressing cancer, or inhibiting cancer metastasis, comprising administering an effective amount of a plant fermentation extract to a mammal, wherein the plant fermentation extract comprises a yeast that is viable in an environment at pH 1, and that is capable of forming spores in a complete medium, wherein the plant fermentation extract is obtained by extraction of plant raw material by osmotic pressure using brown sugar and fermentation of the plant extract with the yeast, wherein the plant raw material comprises cabbage, carrot, celery, ginger and garlic, and wherein the yeast belongs to the genus *Saccharomyces cerevisiae*.

2. The method according to claim 1, wherein the plant raw material further comprises turnip, squash, cauliflower, kale, Japanese mustard spinach, zucchini, Japanese white radish, onion, bok choy, Chinese chive, leek, parsley, broccoli, potherb mustard, and Brussels sprout.

3. The method of claim 2, wherein the yeast has a spore-forming rate of at least 70% when cultured in the complete medium.

4. The method of claim 3, wherein the complete medium comprises a YPD medium.

5. The method of claim 1, wherein the yeast has a spore-forming rate of at least 70% when cultured in the complete medium.

6. The method of claim 5, wherein the complete medium comprises a YPD medium.

\* \* \* \* \*